(12) United States Patent
Bondi et al.

(10) Patent No.: US 6,368,580 B1
(45) Date of Patent: Apr. 9, 2002

(54) COMPOSITION SUITABLE AS FOOD INTEGRATOR AND FOR THE TREATMENT OF INTESTINAL DISORDERS AND ALTERATIONS OF THE BACTERIAL FLORA

(75) Inventors: Moreno Bondi; Paola Messi, both of Modena; Giuliano Frigerio, Milan; Danila Ingrid Marchioretto, Milan; Valter Gatti, Milan, all of (IT)

(73) Assignee: Giuliani S.p.A, Milan (IT)

( * ) Notice: Subject to any disclaimer, the term of this patent is extended or adjusted under 35 U.S.C. 154(b) by 0 days.

(21) Appl. No.: 09/477,062

(22) Filed: Jan. 3, 2000

(30) Foreign Application Priority Data

Jan. 14, 1999 (IT) .......................................... MI99A0050

(51) Int. Cl.$^7$ ................................................. A61K 7/04
(52) U.S. Cl. .................... 424/61; 426/93.46; 435/252.5
(58) Field of Search ................................. 435/832, 853, 435/252.5, 252.9, 244; 426/61, 72, 71, 656; 424/93.45, 93.46

(56) References Cited

PUBLICATIONS

Folia Microbiologica, vol. 20, pp. 46–51, Jan. 1995.

Indian J. Exp. Biol. 14(6), pp. 731–733, Jan. 1976.

*Primary Examiner*—Keith Hendricks
(74) *Attorney, Agent, or Firm*—Hedman & Costigan, P.C.

(57) ABSTRACT

The subject of the present invention is a composition suitable as food integrator and for the treatment of intestinal disorders and alterations of the bacterial flora, characterized in that it contains as active principle a combination of *Bacillus coagulans* and lysine. A further subject of the present invention is a method for the growth and development of cultures of *Bacillus coagulans* in the presence of lysine, as well as the use of these bacterial cultures thus produced and developed in the preparation of compositions suitable both as food integrators and as pharmaceutical compositions.

7 Claims, 2 Drawing Sheets

COMPOSITION SUITABLE AS FOOD INTEGRATOR AND FOR THE TREATMENT OF INTESTINAL DISORDERS AND ALTERATIONS OF THE BACTERIAL FLORA

BACKGROUND OF THE INVENTION

Various metabolic processes take place in the intestine and fall into two basic categories: metabolic processes that involve hydroelectric interchanges between lumen, tissue fluids and blood, as well as the absorption of terminal fractions of the various primary metabolic processes (glucides, proteids, and lipids), or reabsorption of substances relating to the enterohepatic circulation involving detoxication processes (e.g. bile salts); and, metabolic processes that regulate the production of toxic factors and systems responsible for their elimination. Particularly important because of their toxic potential is the production of ammonium radicals (which are extremely harmful to cerebral structures) as terminal processes of nitrogenated metabolism and the production of potentially carcinogenic substances, etc. The intestinal bacterial flora perform a role of enormous importance in the numerous biochemical processes that take place in the intestine. The bio-enzymatic activities of this flora bring about important metabolic modifications of the substrates with which they come into contact.

Gastrointestinal bacterial flora degrade a number of food substrates that cannot be attacked or digested by the digestive enzymes of the organism.

Responsibility for many of the events that are toxic for the organism and responsibility for the phenomena that lie at the basis of aging is attributed to the formation of free radicals, ubiquitous in various tissues of the organism. The formation of free radicals in the colon is particularly marked resulting from biological intervention of the intestinal bacterial flora.

A balance between the production of free radicals and anti-oxidant biological mechanisms is vital for maintenance of a state of health. Ideally, an increase in the production of free radicals ought to be matched by an increase in the processes of detoxication. Instead, aging results in a reduction in the efficiency of these processes. Numerous research studies have been dedicated to the development of probiotic products capable of regulating the activity of the gastrointestinal tract when alterations occur in resident bacterial flora; most commonly caused by: antibiotic usage, excessive sugar and yeast, stress, and processed foods. These products are intended to colonize the gastrointestinal tract with flora and prevent colonization of pathogenic bacteria (e.g. *Candida albicans*). Their mechanism of action involves the production of lactic acid which creates an environment unfavorable to the overgrowth of potentially pathogenic fungi and bacteria (including putrefactive bacteria) and establishment of an aciduric flora However, a number of difficulties have arisen concerning the various biological principles and preparations containing them pertaining to their gastroresistance and stability, elements that affect the culture or development of the active principle in the intestinal tract and its biological activities.

Indeed, various experimental evidence points to the fact that products lose microbial content prior to expiration and log losses occur with limited (even a few hours) exposure in an acidic-pH environment. Thus, both product shelf-life and gastric barrier acidity represent obstacles to an adequate intestinal microbial installation. The lactoproducing microorganisms (i.e., those producing lactic acid, $L^+$) are most commonly used (e.g. mild ferments). They possess probiotic activity and documented tolerability since frequently they are "orthobiotic" flora, i.e., normal human flora. In view of this fact, it is an object of the present invention to introduce such microorganisms into man in higher quantities as integrators in order to prepare the organism to better meet physiological challenges (e.g., intense physical or intellectual activity, physiological cycles, etc.) or even pathological conditions, i.e., for prophylaxis.

The use of lactoproducing microorganisms and the production of commercial preparations containing such principles require optimal growth of the microorganism and biological activity in man.

Requisites for clinical efficacy include stability of the biological product in suitable conditions of preservation (possibly at room temperature), resistance to gastric acidity, and the capacity to promote intestinal growth of the microorganism, together with all the associated characteristic activities.

DETAILED DESCRIPTION OF THE INVENTION

Figure 1:
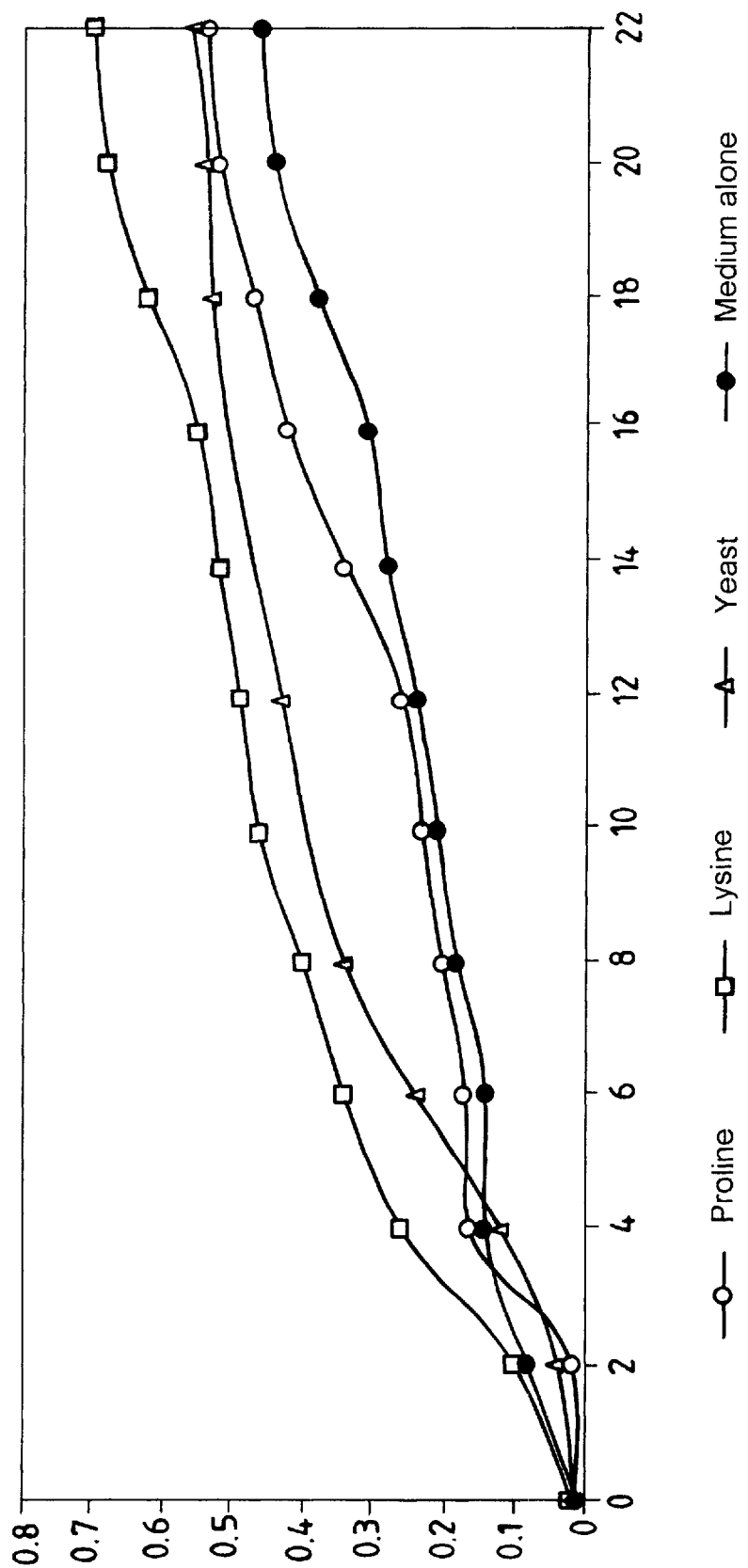
FIG. 1 shows the optical density proportional to bacteria produced over time.

In this regard, the present invention proposes a composition that is suitable both as a food integrator and for the treatment of intestinal disorders and alterations of bacterial flora, containing a combination of *Bacillus coagulans* and lysine as active components. Surprisingly, we find that lysine acts as a growth enhancer for the lactoproducing *Bacillus coagulans*.

In one embodiment of the present invention, the combination is made by associating the aforesaid two components as such.

In an alternative embodiment of the invention, the combination of the active principle is made by first subjecting the *Bacillus coagulans* to a culture containing lysine in the germinative phase, and then culturing to the spore state.

In the latter embodiment of the invention, the *Bacillus coagulans* thus subjected to the culture gives rise to a modified form of the starting bacterium, a form not described in the existing literature. According to this embodiment of the invention, the active principle consists of a new bacterial strain of *Bacillus coagulans* in which lysine is incorporated in the growth phase. A culture of this new microorganism was therefore deposited at the qualified center for culture collection, DSMZ (Deutsche Sammlung von Mikroorganismen und Zellkulturen GmbH) (German Collection of Microorganisms and Cell Cultures) on Jul. 17, 1998. The registration number of the culture thus filed is DSM 12316 (bacterial strain LAB LYS98).

In a further embodiment of the invention, the active principle results from the combination of the aforesaid bacterial strain (DSM 12316) and lysine. According to the present invention, the bacterial strain of the sporogenous lactobacillus type, *Bacillus coagulans* (otherwise defined in the literature as *Lactobacillus sporogenes*), ensures both stability in the external environment (even at temperatures of 40 C. for various months and pf 60 C.–90 C. for 30 minutes) and resistance to gastric acidity after administration, as well as high bioavailability in subsequent portions of the intestine.

The bacterial strain in question is a Gram-positive aerobic and micro-aerophilic bacillus of dimensions ranging between 0.6–1 µm and 2.5–5 µm, which moves by means of flagella, with morphology that is typical of Lactobacilli (individual bacilli or, more rarely, bacilli arranged in short chains, the length of which varies according to culture conditions). For this reason, it is included in the genus Lactobacillus in the 5th edition of *Bergey's Manual of Determinative Bacteriology*. Its taxonomic placing was, however, modified in the 7th edition of *Bergey's Manual of Determinative Bacterology* for reasons of simplicity of classification, given that it produces spores which appear under microscopic observation as refractive subterminal/terminal ellipsoidal bodies of dimensions ranging between 0.9–1.2 µm and 1.0–1.7 µm. Not all authors are, however, in agreement on this form of classification given that there does not appear to be any documented likeness between the two microorganisms.

According to this criterion, other catalase-positive aerobic or facultative sporogenous bacilli producing lactic acid are assigned to the genus Bacillus in the 8th edition of *Bergey's Manual of Determinative Bacteriology*. Despite the taxonomic reference, the name *Bacillus sporogenes* is widely used for this bacterium.

From the biological point of view, *Bacillus coagulans* grows at a temperature of 35–50 C. at a pH preferably of between 5.5 and 6.5.

The elective culture medium is "GYE agar medium", where the bacterium develops forming colonies of irregular shape, with lobate margins and umbonate profiles. In the broth formulation itself, growth takes the form of a surface film (area of contact with oxygen), associated with a slight diffused turbidity, while in the broth cultures that undergo stirring the growth presents just diffused turbidity.

Among the properties and characteristics that are of importance from the standpoint of use of this biological principle in man, the following are emphasized: the capacity to multiply, the capacity to adhere at a cellular level and to produce lactic acid L$^+$ in significant quantities as well as bacteriocins (or similar substances) against various bacterial species, including those unrelated taxonomically including enterpathogenic germs. *Bacillus coagulans* or *Lactobacillus sporogenes* in the vegetative phase is insensitive/resistant to numerous chemobiotics, such as penicillin, cephalosporins, lincomycin, sulfamethizole, trimethoprim-sulfamethoxazole, etc.

It is an object of the present invention to verify which culture media prove most suitable for guaranteeing optimal growth of *Bacillus coagulans* once they have passed to the vegetative phase, and are compatible with human alimentation.

Consequently, microbiological tests have been conducted by adding a number of amino acids (particularly aspartic acid, lysine, proline) to the culture medium specific for Lactobacillus. From these experiments we discovered, according to the invention, that the addition of lysine in certain given concentrations (of the order of 0.1–1 mg/ml) to the medium enhanced the growth of the Lactobacillus cells and the formation of lactic acid (L$^+$), a phenomenon which does not occur, or occurs only to a decidedly modest extent with other amino acid nutrilites. Evaluation of the growth of *Bacillus coagulans* was performed using and agar/Sabouraud's broth to which 0.5% of yeast extract was added. At this point, an attempt was made to determine which of the various amino acid components present in the yeast (aspartic acid, proline, lysine, tryptophan), and in what concentrations, were able to favor more vigorous development of the microorganism. The increase in growth was evaluated by biophotometer which recorded the optical density ($A_{630}$). After a set of preliminary evaluations, two amino acids which yielded the best results (i.e., lysine and proline) were selected and compared according to the following method.

Example A

In special sterilized cuvettes for biophotometry, broth cultures were prepared, with the addition to the base culture medium (10 ml of Sabouraud's broth) of:

a) lysine, 0.025 mg/ml; b) proline, 0.01 mg/ml; and c) yeast, 5 mg/ml.

One cuvette containing Sabouraud's broth alone was used as control. Each of the four broth cultures was subsequently inoculated with 100 µl of a dilution of a broth culture (overnight incubation) of *Bacillus coagulans* made starting from the lyophilized powder (final concentration of $10^4$ cfu/ml).

The growth of the culture was evaluated in terms of optical density, using a biophotometer, which is capable of determining the degree of development on the basis of the increase in turbidity. The curvettes thus prepared were set inside the compartment of the instrument in the presence of a magnetic stirrer that was able to keep the culture in uniform suspension, a condition which enables a proper reading of the turbidity of the culture medium to be made.

The graph appearing in FIG. 1 of the drawings attached to the present description summarizes the results of this test. The optical density appears on the ordinate, the values proportional to the number of bacteria produced. The time is given on the abscissa. The four curves shown on the graph identify the behavior, respectively, of lysine (at a concentration of 0.025 mg/ml), yeast (5 mg/ml), proline (0.01 mg/ml), and the Sabouraud's culture medium reference standard.

From a comparison of the growth curves obtained after overnight incubation at 37° C., the most effective nutrient was lysine (at a concentration of 0.025 mg/ml).

In fact, lysine significantly increases the growth curve, reducing the latency phase and increasing the number of cells present at the various times considered.

Also, lactic acid (L$^+$) production, carried out on a 24-hour broth culture to which lysine was added, proved higher (reaching concentrations of 486 mg/l) as compared to blank controls or after the addition of other amino acids.

Example B

An experiment was conducted, in which *Bacillus coagulans* was grown in culture media containing lysine in three successive stages:

Stage I: growth of the vegetative form in a liquid medium (Sabouraud's broth+lysine 0.25 mg/ml, i.e., at a concentration ten times higher than that resulting in the best yield in the test of Example A);

Stage II: subculture, with overnight incubation at 37° C., in solid culture medium (Sabouraud's agar with addition of the amino acid lysine at the same concentration to enable its further incorporation);

Stage III: further incubation of the plates at room temperature for a sufficient period of time to cause evident morphological changes of the colonies, which, from having an umbonate and mucous appearance, became flat and dry following gradual sporulation of the microorganism.

The microorganism thus obtained presents characteristics that are new with respect to the starting bacterium. It is a new form in which the lysine has been intracellularly incorporated by *Bacillus coagulans* in its growth form. This new biological preparation has been registered at DSMZ under the code DSM 12316 (LAB LYS98). Verification of the increase in growth of the new form DSM 12316 compared to the starting *Bacillus coagulans* was conducted by evaluating the development of the two strains under examination at the biophotometer according to the procedure described previously.

Figure 2:
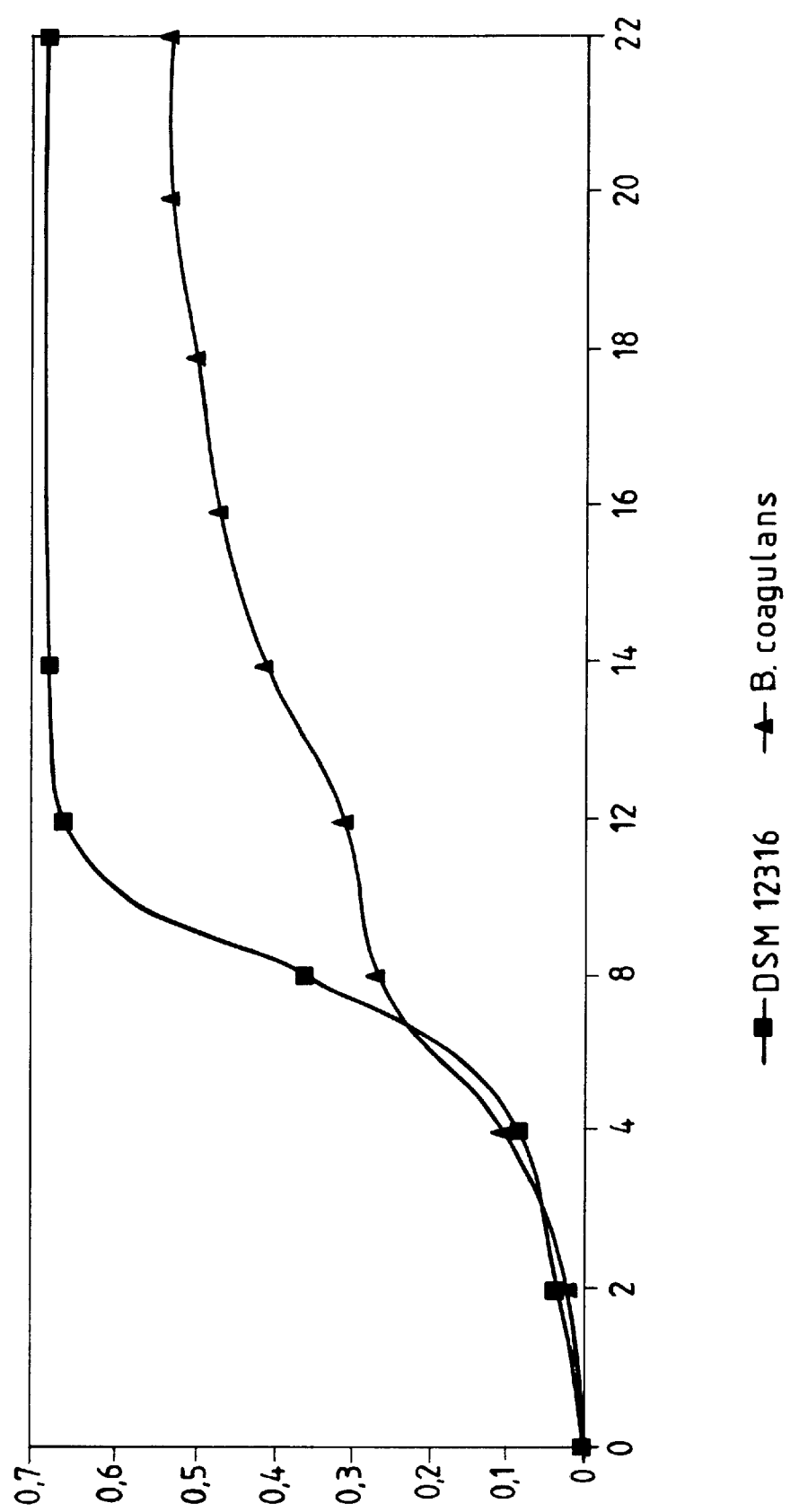
FIG. 2 shows the growth comparison of the starting *Bacillus coagulans*, versus DSM 12316.

The graph presented in FIG. 2 of the attached drawings shows the comparison of the growth curves recorded after overnight incubation at 37° C.

Once again, optical density appears on the ordinate, and time is given on the abscissa.

The two curves refer, respectively, as pointed out in the caption of FIG. 2, to the growth of *Bacillus coagulans* and of DSM 12316 in Sabouraud's broth to which lysine had been added (concentration 0.025 mg/ml).

As may be seen from FIG. 2, starting from 8–12 hours, the growth curve becomes markedly more advantageous in terms of optical density, and hence bacterial growth, as compared to the simple combination of *Bacillus coagulans* and lysine as such.

In general, the pharmaceutical or nutritional compositions to which the present invention refers may preferably be of the following types:

a) preparations of *Bacillus coagulans* with the addition of lysine in coated formulations to enable a delayed release of the amino acid in the intestinal tract;

b) preparations of *Bacillus coagulans* pre-cultured in culture media enriched with lysine, in particular preparations of the culture DSM 12316 specified above;

c) preparations comprising the said a) and b) together; and d) preparations as per a), b) and c), integrated with other components, among which activated carbon, various micronutrients, and natural antioxidants, such as oleoeuropein or phenylpropanoids of Ajuga reptans, possibly with appropriate coatings designed to control release into the gastrointestinal tract.

The other components according to d) comprise vitamins, particularly vitamins with specific antioxidant action (e.g. vitamins A, C, and E) and B vitamins, various mineral salts of oligo-elements, the intake levels of which are recommended on the basis of specific studies (particularly those linked to mechanisms of detoxication of the accumulation of free radicals, such as copper, zinc, manganese, selenium, magnesium, etc.), various nucleic fractions and enzymes present, as such or in mixed form, in extractive nutriment.

The range of nutritional principles envisaged is not limiting since it may comprise both compounds/products of an orthomolecular type (i.e., already forming part of the human organism, as is the case of the majority of substances listed above), and non-orthomolecular products of natural origin, whether vegetable or animal, but in all cases having the character of nutraceutic nutriment, i.e., with a specific scientific connotation in relation to particular metabolic steps.

The non-caloric micronutrients (nutraceutic nutriment) already considered, and probably also others, normally play a role in systemic biochemical processes and perform physiological functions for maintaining a state of health. Since they may not reveal any visible effect, they may not be recognized for their biological significance). According to the invention, compositions can be prepared to release active principles into distal regions of the intestine to prevent early absorption.

The "nutriment/vehicle" may comprise any foodstuff which resists degradation in the proximal intestinal regions, englobing, in technologically suitable preparations, the micronutritional principles referred to and releasing them primarily in the colon for better utilization.

An indicative, but not exclusive list of macromolecules which may be indigestible or poorly digested by the gastrointestinal juices, but which are potentially degradable by the enzymatic activity of intestinal bacterial flora, and allowed by current legislation governing foodstuffs is the following: microcrystalline cellulose, methylcellulose, hydroxypropyl cellulose, hydroxypropyl methylcellulose, methylethylcellulose, carboxymethylcellulose, xanthan gum, gum lac, hydrogenated vegetable fats, and pectin. From the standpoint of food technology, different solutions may be envisaged. One example is a core of varying shape containing the nutritional substance to be vehicled, obtained by standard tablet manufacturing technology, coated with a protective layer consisting of adjuvants allowed by current legislation governing foodstuffs, which prevents contact of the core with the gastro-duodenal tract. For this layer, insoluble or only slightly soluble substances may be used (e.g. gelatinizing substances, gelatin, hydrogenated food-containing fats). The desired effect is obtained by means of mechanical erosion, and the thickness of the layer is the factor that determines release of the active principle in the colon or in the distal region of the intestine.

It was also noted that the use of macromolecules having a base of indigestible fibers, primarily of natural vegetable origin, normally useful for favoring the formation of a voluminous and soft fecal mass, i.e., a physiological fecal mass, surprisingly increased the "nutraceutic" action of a whole series of compounds that fall within the sphere of the essential noncaloric micronutrients when said nutraceutics were technologically englobed in these macromolecular complexes.

EXAMPLES OF FORMULATION

For a better understanding of the characteristics of the compositions of the invention, examples of practical embodiment follow. These examples have a purely illustrative and nonlimiting purpose as forms for administration.

1) hard gelatin capsules containing *Bacillus coagulans* (or the new strain LAB LYS98 as defined above) to the amount of 10–1000 million cfu per capsule, and 10 mg up to 100 mg of lysine in the form of microgranules coated for delayed controlled release;

2) sachets containing powder or granulate;

3) flasks with powder or granulate and a dosing measure; and 4) small drinking flasks.

EXAMPLE 1

HARD GELATIN CAPSULES

Composition

| Description | Quantity | |
|---|---|---|
| *Bacillus coagulans* or LAB LYS98 | 100(10 – 1000*10$^5$ cfu) | mg |
| L-Lysine hydrochloride (in the gastro-enteroprotected form) | 0-25-250 | mg |

-continued

| Description | Quantity | |
|---|---|---|
| Magnesium stearate | 4.4 | mg |
| Colloidal silica | 0.8 | mg |
| Dextrose | up to 440 | mg |
| Hard gelatin capsule | 97 | mg |

EXAMPLE 2

POWDER IN FLASK WITH DOSING MEASURE

Composition for 100 g of powder

| Description | Quantity | |
|---|---|---|
| *Bacillus coagulans* or LAB LYS98 | 100(10 – 1000*$10^5$ cfu) | mg |
| L-Lysine hydrochloride (in the gastro-enteroprotected form) | 0-25-250 | mg |
| Vitamin B1 | 1.8 (128% RDA) | mg |
| Vitamin B2 | 2.4 (150% RDA) | mg |
| Vitamin B6 | 3 (150% RDA) | mg |
| Vitamin PP | 27 (150% RDA) | mg |
| Pantothenic acid | 8.28 (138% RDA) | mg |
| Folic acid | 0.3 (150% RDA) | mg |
| Dextrin | 25 | g |
| Dextrose | up to 100 | g |

EXAMPLE 3

FLASK WITH DOSING CAP

Composition of contents of dosing cap

| Description | Quantity | |
|---|---|---|
| *Bacillus coagulans* or LAB LYS98 | 100(10 – 1000*$10^5$ cfu) | mg |
| L-Lysine hydrochloride (in the gastro-enteroprotected form) | 0-25-250 | mg |
| Vitamin B1 | 1.8 (128% RDA) | mg |
| Vitamin B2 | 2.4 (150% RDA) | mg |
| Vitamin B6 | 3 (150% RDA) | mg |
| Vitamin PP | 27 (150% RDA) | mg |
| Pantothenic acid | 8.28 (138% RDA) | mg |
| Folic acid | 0.3 (150% RDA) | mg |
| Maltodextrins | up to 500 | mg |

Composition of contents of flask

| Description | Quantity | |
|---|---|---|
| Fructo-oligosaccharides | 4 | g |
| Sodium benzoate | 0.01 | g |
| Citric acid | 0.02 | g |
| Sodium phosphate | 0.01 | g |
| Flavoring | 0.02 | g |
| Depurated water | up to 10 | mL |

EXAMPLE 4

GRANULATE IN SACHETS

Composition per sachet

| Description | Quantity | mg |
|---|---|---|
| *Bacillus coagulans* or LAB LYS98 | 100(10 – 1000*$10^5$ cfu) | mg |
| L-Lysine hydrochloride (in the gastro-enteroprotected form) | 0-25-250 | mg |
| Vitamin B1 | 1.8 (128% RDA) | mg |
| Vitamin B2 | 2.4 (150% RDA) | mg |
| Vitamin B6 | 3 (150% RDA) | mg |
| Vitamin PP | 27 (150% RDA) | mg |
| Pantothenic acid | 8.28 (138% RDA) | mg |
| Folic acid | 0.3 (150% RDA) | mg |
| Mannitol | 150 | mg |
| Sodium benzosulphimide | 10 | mg |
| Xanthan rubber | 100 | mg |
| Natural flavoring | 100 | mg |
| Sorbitol | up to 3000 | mg |

EXAMPLE 5

INDIVIDUAL OR COMBINED CAPSULES

Composition of capsule with *Bacillus coagulans*/ *Lactobacillus sporogenes* or LAB LYS98

| Description | Quantity | |
|---|---|---|
| *Bacillus coagulans* or LAB LYS98 | 100(10 – 1000*$10^5$ cfu) | mg |
| L-lysine hydrochloride (in the gastroprotected form) | 0-25-250 | mg |
| Vitamin B1 | 1.8 (128% RDA) | mg |
| Vitamin B2 | 2.4 (150% RDA) | mg |
| Vitamin B6 | 3 (150% RDA) | mg |
| Vitamin PP | 27 (150% RDA) | mg |
| Pantothenic acid | 8.28 (138% RDA) | mg |
| Folic acid | 0.3 (150% RDA) | mg |
| Magnesium stearate | 4.4 | mg |
| Colloidal silica | 0.8 | mg |
| Dextrose | up to 440 | mg |
| Hard gelatin capsule | 97 | mg |

Composition of capsule with carbon

| Description | Quantity | |
|---|---|---|
| Activated carbon | 150 | mg |
| Hard gelatin capsule in gastroresistant form | 140 | mg |

What is claimed is:

1. A composition for oral use as a food integrator and for the treatment of intestinal disorders or alterations of gastrointestinal bacterial flora, comprising an effective amount of a bacterial strain of *Bacillus coagulans* which is registered under accession No. DSM 12316, in association with a physiologically acceptable carrier.

2. The composition according to claim 1, further comprising lysine.

3. The composition according to claim 2, wherein said lysine is protected by a gastro-protective coating to achieve a delayed release of the lysine in the intestinal tract.

4. The composition according to claim 1 further comprising an ingredient selected from the group consisting of vitamins, oligoelements, mineral salts, anti-oxidants of vegetable origin, activated carbon and mixtures thereof.

5. The composition according to claim 1, comprising a gastro-protective coating for releasing said *Bacillus coagulans* into distal regions of an intestine of a human.

6. The composition according to claim 1, wherein said physiological substance is a nutritional substance.

7. A method for treating intestinal disorders or alterations of gastrointestinal bacterial flora, comprising the administration to a subject in need of treatment of an effective amount of a composition including a bacterial strain of *Bacillus coagulans* registered under accession No. 12316, in association with a physiologically acceptable carrier.

* * * * *